United States Patent
Olson et al.

(10) Patent No.: US 8,695,591 B2
(45) Date of Patent: Apr. 15, 2014

(54) APPARATUS AND METHOD OF MONITORING AND RESPONDING TO RESPIRATORY DEPRESSION

(76) Inventors: Lloyd Verner Olson, Colorado Springs, CO (US); Elizabeth Ann Olson, Colorado Springs, CO (US)

( * ) Notice: Subject to any disclaimer, the term of this patent is extended or adjusted under 35 U.S.C. 154(b) by 260 days.

(21) Appl. No.: 12/946,698

(22) Filed: Nov. 15, 2010

(65) Prior Publication Data

US 2011/0290250 A1 Dec. 1, 2011

Related U.S. Application Data

(60) Provisional application No. 61/348,354, filed on May 26, 2010, provisional application No. 61/352,480, filed on Jun. 8, 2010, provisional application No. 61/372,404, filed on Aug. 10, 2010.

(51) Int. Cl.
*A61M 16/00* (2006.01)

(52) U.S. Cl.
USPC ............ 128/203.14; 128/203.12; 128/203.13; 600/323

(58) Field of Classification Search
USPC ............. 128/200.24, 203.12–203.18, 204.23; 604/65–67, 131, 151; 600/323
See application file for complete search history.

(56) References Cited

U.S. PATENT DOCUMENTS

| | | | |
|---|---|---|---|
| 4,280,494 A * | 7/1981 | Cosgrove et al. | 604/503 |
| 5,836,300 A | 11/1998 | Mault | |
| 5,857,460 A | 1/1999 | Popitz | |
| 5,957,885 A | 9/1999 | Bollish et al. | |
| 6,002,133 A | 12/1999 | Nelson et al. | |
| 6,076,392 A | 6/2000 | Drzewiecki | |
| 6,099,481 A | 8/2000 | Daniels et al. | |
| 6,131,571 A | 10/2000 | Lampotang et al. | |
| 6,135,107 A | 10/2000 | Mault | |
| 6,179,784 B1 | 1/2001 | Daniels et al. | |
| 6,216,692 B1 | 4/2001 | Todokoro et al. | |
| 6,250,132 B1 | 6/2001 | Drzewiecki | |
| 6,272,905 B1 | 8/2001 | Drzewiecki | |
| 6,305,212 B1 | 10/2001 | Drzewiecki | |
| 6,309,360 B1 | 10/2001 | Mault | |
| 6,327,497 B1 | 12/2001 | Kirchgeorg et al. | |
| 6,379,312 B2 | 4/2002 | O'Toole | |
| 6,471,658 B1 | 10/2002 | Daniels et al. | |

(Continued)

FOREIGN PATENT DOCUMENTS

| | | |
|---|---|---|
| GB | 2187845 | 9/1987 |
| WO | WO 2007/147505 | 12/2007 |
| WO | WO 2010/093677 | 8/2010 |

OTHER PUBLICATIONS

International Search Report for International (PCT) Patent Application No. PCT/US2011/024977, mailed May 6, 2011 2 pages.

(Continued)

*Primary Examiner* — Loan H Thanh
*Assistant Examiner* — Andrew S Lo
(74) *Attorney, Agent, or Firm* — Sheridan Ross P.C.

(57) ABSTRACT

The present disclosure involves a system for monitoring patients, and more specifically post-operative patients receiving narcotics, and a novel apparatus for automatically delivering a narcotic-reversing agent, including but not limited to the agent commonly known as naloxone, in response to dangerous respiratory conditions such as respiratory depression or other undesired consequences caused by reaction to narcotic dosage.

19 Claims, 3 Drawing Sheets

(56) References Cited

U.S. PATENT DOCUMENTS

| | | |
|---|---|---|
| 6,512,581 B1 | 1/2003 | Yamamori et al. |
| 6,572,561 B2 | 6/2003 | Mault |
| 6,579,592 B1 | 6/2003 | Matsubaguchi et al. |
| 6,615,744 B1 | 9/2003 | Eckstein et al. |
| 6,616,615 B2 | 9/2003 | Mault |
| 6,629,934 B2 | 10/2003 | Mault et al. |
| 6,709,403 B1 | 3/2004 | Ratner |
| RE38,533 E | 6/2004 | Kirchgeorg et al. |
| 6,745,764 B2 | 6/2004 | Hickle |
| 6,807,965 B1 | 10/2004 | Hickle |
| 6,848,444 B2 | 2/2005 | Smith et al. |
| 6,851,427 B1 | 2/2005 | Nashed |
| 6,874,502 B1 | 4/2005 | Nashed |
| 6,876,303 B2 | 4/2005 | Reeder et al. |
| 6,938,619 B1 | 9/2005 | Hickle |
| 6,986,347 B2 | 1/2006 | Hickle |
| 7,032,522 B2 | 4/2006 | George et al. |
| 7,038,588 B2 | 5/2006 | Boone et al. |
| 7,040,315 B1 | 5/2006 | Stromberg |
| 7,054,680 B1 | 5/2006 | Genger et al. |
| 7,077,135 B2 | 7/2006 | Pagan |
| 7,081,095 B2 | 7/2006 | Lynn et al. |
| 7,152,604 B2 | 12/2006 | Hickle et al. |
| 7,154,397 B2 | 12/2006 | Zerhusen et al. |
| 7,201,734 B2 | 4/2007 | Hickle |
| 7,247,154 B2 | 7/2007 | Hickle |
| 7,255,671 B2 | 8/2007 | Boone et al. |
| 7,308,894 B2 | 12/2007 | Hickle |
| 7,311,657 B2 | 12/2007 | Boone et al. |
| 7,314,010 B2 | 1/2008 | George et al. |
| 7,316,231 B2 | 1/2008 | Hickle |
| 7,357,772 B2 | 4/2008 | McDermott |
| RE40,365 E | 6/2008 | Kirchgeorg et al. |
| 7,398,115 B2 | 7/2008 | Lynn |
| 7,443,302 B2 | 10/2008 | Reeder et al. |
| 7,445,602 B2 | 11/2008 | Yamamori et al. |
| 7,455,644 B2 | 11/2008 | Yamamori et al. |
| 7,516,740 B2 | 4/2009 | Meier |
| 7,530,353 B2 | 5/2009 | Choncholas et al. |
| 7,539,537 B2 | 5/2009 | Hickle |
| 7,540,243 B2 | 6/2009 | George et al. |
| 7,556,036 B2 | 7/2009 | Bouillon et al. |
| 7,562,657 B2 | 7/2009 | Blanch et al. |
| 7,565,905 B2 | 7/2009 | Hickle |
| 7,610,094 B2 | 10/2009 | Stahmann et al. |
| 7,662,106 B2 | 2/2010 | Daniels et al. |
| 7,668,731 B2 | 2/2010 | Martucci et al. |
| 7,679,520 B2 | 3/2010 | Zerhusen et al. |
| 7,766,857 B2 | 8/2010 | Tham et al. |
| 7,774,060 B2 | 8/2010 | Westenskow |
| 7,833,213 B2 | 11/2010 | Katz |
| 7,848,794 B2 | 12/2010 | Genger |
| 7,911,349 B2 | 3/2011 | Zerhusen |
| 2002/0014951 A1 | 2/2002 | Kramer et al. |
| 2002/0044059 A1 | 4/2002 | Reeder et al. |
| 2002/0139368 A1 | 10/2002 | Bachinski |
| 2003/0079746 A1* | 5/2003 | Hickle ............... 128/203.12 |
| 2003/0106553 A1 | 6/2003 | Vanderveen |
| 2003/0130567 A1 | 7/2003 | Mault et al. |
| 2003/0130595 A1 | 7/2003 | Mault |
| 2003/0135087 A1 | 7/2003 | Hickle et al. |
| 2003/0209242 A1 | 11/2003 | Hickle |
| 2004/0034287 A1 | 2/2004 | Hickle |
| 2004/0254501 A1 | 12/2004 | Mault |
| 2005/0039742 A1 | 2/2005 | Hickle |
| 2005/0066968 A1 | 3/2005 | Shofner et al. |
| 2005/0112325 A1 | 5/2005 | Hickle |
| 2005/0126562 A1 | 6/2005 | Rabinowitz et al. |
| 2005/0177056 A1 | 8/2005 | Giron et al. |
| 2005/0177096 A1 | 8/2005 | Bollish et al. |
| 2005/0182389 A1 | 8/2005 | Laporte et al. |
| 2006/0093785 A1 | 5/2006 | Hickle |
| 2006/0249155 A1 | 11/2006 | Gambone |
| 2006/0253045 A1 | 11/2006 | Coifman |
| 2006/0283450 A1 | 12/2006 | Shissler et al. |
| 2007/0062532 A1 | 3/2007 | Choncholas |
| 2007/0062533 A1 | 3/2007 | Choncholas et al. |
| 2007/0089744 A1 | 4/2007 | Wiese |
| 2007/0095347 A1 | 5/2007 | Lampotang et al. |
| 2007/0213658 A1 | 9/2007 | Hickle |
| 2007/0277823 A1 | 12/2007 | Al-Ali et al. |
| 2007/0299389 A1 | 12/2007 | Halbert et al. |
| 2008/0011294 A1 | 1/2008 | Heesch et al. |
| 2008/0021379 A1 | 1/2008 | Hickle |
| 2008/0091117 A1 | 4/2008 | Choncholas et al. |
| 2008/0097168 A1 | 4/2008 | Hopermann et al. |
| 2008/0127977 A1 | 6/2008 | Orr et al. |
| 2008/0171762 A1 | 7/2008 | Ockert |
| 2008/0178880 A1 | 7/2008 | Christopher et al. |
| 2008/0202521 A1 | 8/2008 | Mitton et al. |
| 2008/0202522 A1 | 8/2008 | Mitton et al. |
| 2008/0202523 A1 | 8/2008 | Mitton et al. |
| 2008/0202524 A1 | 8/2008 | Mitton et al. |
| 2008/0202525 A1 | 8/2008 | Mitton et al. |
| 2008/0214948 A1 | 9/2008 | Myklebust et al. |
| 2008/0230060 A1 | 9/2008 | Tham |
| 2008/0230061 A1 | 9/2008 | Tham |
| 2008/0230062 A1 | 9/2008 | Tham |
| 2008/0230064 A1 | 9/2008 | Tham |
| 2008/0230065 A1 | 9/2008 | Heinonen |
| 2008/0236581 A1 | 10/2008 | Rantala et al. |
| 2009/0020127 A1 | 1/2009 | Boone et al. |
| 2009/0096615 A1 | 4/2009 | Reeder et al. |
| 2009/0114224 A1 | 5/2009 | Handzsuj et al. |
| 2009/0143996 A1 | 6/2009 | Karlsson et al. |
| 2009/0159079 A1 | 6/2009 | Meier |
| 2009/0203974 A1 | 8/2009 | Hickle |
| 2009/0205654 A1 | 8/2009 | Bouillon |
| 2009/0241807 A1 | 10/2009 | George et al. |
| 2009/0241954 A1 | 10/2009 | Karlsson |
| 2009/0277447 A1 | 11/2009 | Voss et al. |
| 2009/0293877 A1 | 12/2009 | Blanch et al. |
| 2009/0299430 A1 | 12/2009 | Davies et al. |
| 2009/0314290 A1 | 12/2009 | Hickle |
| 2009/0318805 A1 | 12/2009 | Raphael |
| 2010/0083968 A1 | 4/2010 | Wondka et al. |
| 2010/0093800 A1 | 4/2010 | Hickle |
| 2010/0097380 A1 | 4/2010 | Daniels et al. |
| 2010/0106037 A1 | 4/2010 | Kacmarek et al. |
| 2010/0145165 A1 | 6/2010 | Merry |
| 2011/0313262 A1* | 12/2011 | Zornow ............... 600/323 |
| 2013/0197430 A1 | 8/2013 | Olson et al. |

OTHER PUBLICATIONS

Written Opinion for International (PCT) Patent Application No. PCT/US2011/024977, mailed May 6, 2011 6 pages.

International Preliminary Report on Patentability for International (PCT) Patent Application No. PCT/US2011/024977, mailed Dec. 6, 2012 8 pages.

International Search Report and Written Opinion for International (PCT) Patent Application No. PCT/US2013/031338 mailed May 21, 2013, 8 pages.

Examination Report for Australia Patent Application No. 2011258819, dated Nov. 6, 2013 6 pages.

Notice of Acceptance for Australia Patent Application No. 2011258819, dated Dec. 6, 2013 2 pages.

* cited by examiner

APPARATUS AND METHOD OF MONITORING AND RESPONDING TO RESPIRATORY DEPRESSION

CROSS REFERENCE TO RELATED APPLICATIONS

This application claims the benefit of U.S. Provisional Patent Application No. 61/348,354, filed on May 26, 2010, and U.S. Provisional Patent Application No. 61/352,480, filed on Jun. 8, 2010, and U.S. Provisional Patent Application No. 61/372,404, filed on Aug. 10, 2010, the entire disclosures of which are incorporated by reference herein in their entireties.

FIELD OF THE INVENTION

The present disclosure relates generally to systems for monitoring the breathing of sedated patients, especially those receiving narcotic/opioid pain medications that depress or endanger normal breathing, and specifically an apparatus that automatically delivers a narcotic reversal agent to restore normal breathing. The apparatus minimizes the delay in rescuing patients with abnormal monitored alarm conditions otherwise at risk of death, irreversible brain damage, or other potentially avoidable outcomes. According to another embodiment disclosed herein, a method for responding to respiratory depression occurring in patients is disclosed.

BACKGROUND OF THE INVENTION

The number and frequency of patient operations throughout the world has increased notably over the past 25 years. Today there are approximately 25 million post-operative patients a year in the U.S. alone. Assuming the average post-operative patient remains in the hospital 2½ days, this correlates to approximately 62.5 million post-op days and a demand of approximately 180,000 independent devices for controlling and monitoring narcotic delivery. Thus, there is an increasing and wide-spread demand for devices, methods, and systems for monitoring and controlling the status of post-operative patients and the effects of narcotics upon the same. In addition, sleep apnea is increasingly being diagnosed, and this expanding patient group is more sensitive to narcotics, creating additional risks and demand for timely treatment of endangered breathing.

A common narcotic delivery device used in patients, usually post-operative patients, is known as the patient-controlled analgesia pump ("PCA pump"). A PCA pump permits the patient to control the dosage of narcotic (typically in response to increased pain) by pressing a button that activates the pump and delivers a certain amount of narcotic. PCA pumps from several manufacturers have been recalled by the FDA because of malfunction, tampering and unknown errors, permitting unsafe doses of narcotics to be delivered in a certain period of time. In efforts to prevent further harm to patients, various companies, agencies, etc. have focused on trying to improve the efficacy of PCA pumps, in an effort to eliminate the possibility of overdose, user error and/or intentional tampering. Despite these efforts, PCA pumps and associated user error have been implicated in deaths from overdose, even in young (ages 21-35 years of age), healthy patients. Despite these efforts, it has become clear that user error and unpredictable patient factors still result in fatal errors and serious complications, and that current narcotic delivery systems still carry a significant risk of patient harm in connection with PCA pumps.

It is also known that post-operative patients and other vulnerable patients, whether or not treated with narcotics, may be at risk for suffering from respiratory-related problems including respiratory depression and sleep apnea. Most PCA pumps and other automated bedside patient monitoring equipment do not supply adequate control or signaling to address these types of problems. For optimal patient care, better monitoring of patients should be mandatory for the timeliest detection of life-threatening respiratory events occurring in post-operative and other vulnerable patients.

Despite whether an automated delivery device (PCA) is employed or not, overdose is a significant risk in all patients. The Anesthesia Patient Safety Foundation, the Institute for Safe Medical Practices, the American College of Surgeons and the Joint Commission of Accreditation for Hospitals have determined that patients given narcotics after surgery are being inadequately monitored and are at risk. Furthermore, hospitalized patients are generally at higher risk for various complications regardless of exposure to narcotics. In a narcotic overdose situation caused by a pump delivery system or human error, optimal monitoring helps care-givers discover a crisis earlier than currently possible, which minimizes critical time-to-treatment. Suboptimal monitoring of differing patient types may result in life-threatening outcomes in post-operative patients given narcotics for pain control. In addition, respiratory depression can lead to stroke, heart attack, brain injury, and death, even in young, healthy patients. If a patient stops breathing, hospital staff or other care providers would prefer to detect it immediately, and common monitoring systems are generally too slow or unresponsive to provide the information necessary to timely respond to respiratory depression (without oxygen, brain death occurs in about three minutes).

To complicate this problem further, most patients are not monitored continuously, but rather simply have a nurse periodically visiting a patient's room to count their respirations. Generally, only patients in an operating room are monitored on a continuous basis with an expert in airway management present (Anesthesiologist). Thus, given these conditions, it is impossible for staff or other care providers to sufficiently monitor patients to prevent disasters outside the operating room. In post-operative and many other patient-care situations, there are substantial risks that complications will arise that require attention within seconds, but, appropriate care and intervention is usually minutes away.

Abnormal breathing and monitoring thereof may provide a valuable indication that serious events are about to occur, have just occurred, or are occurring. Timely warnings can assist in responding to and treating these events as soon as possible to minimize risk of disability or death. Superior monitoring of patients results in better outcomes due to earlier detection of respiratory or breathing-related problems.

Outside of operating rooms, the most commonly used breathing monitor besides occasional visits by staff to count respirations is "pulse oximetry," which has been in existence for over 20 years and has greatly improved the safety of patients. The pulse oximetry apparatus generally consists of a clip-on monitor (typically on a finger or on an earlobe) that detects the amount of oxygen in a patient's blood stream. Unfortunately, when a patient stops breathing, it might take minutes for the oxygen level in their blood stream to drop to a dangerously low level that will be detected with pulse oximetry. Therefore, pulse oximetry is relatively insensitive and slow in detecting a breathing crisis and leaves less time to correct that problem before irreversible damage begins to occur.

Recently, an acoustic monitor (measuring the sound of breathing) has been used with success in patients to detect air movement in and out of the lungs. It may be an alternative to pulse oximetry in the early detection of cessation or slowing of breathing. However, current technology is limited by ambient noise and not recommended for patients less than twelve years old or larger patients with increased adipose tissue.

End-tidal $CO_2$ monitors (capnography) provide the most sensitive means (100% sensitive) for providing the earliest detection of respiratory depression from narcotic overdose and disasters that might follow. "End-tidal" carbon dioxide refers to the amount of carbon dioxide exhaled at the end of a breathing cycle. An end-tidal monitor operates on the principle that if sufficient carbon dioxide is not being exhaled, sufficient oxygen is similarly not being inhaled—an obviously life-threatening situation that requires adequate monitoring for hospital and post-hospital settings. These types of $CO_2$ monitors have been used for anesthesia monitoring during surgery and increasingly for intensive care monitoring, emergency departments and in ambulances.

SUMMARY OF THE INVENTION

The present disclosure involves a system for monitoring patients, and more specifically post-operative patients receiving narcotics, and a novel apparatus for automatically delivering a narcotic-reversing agent, including but not limited to the agent commonly known as naloxone, in response to dangerous respiratory conditions such as respiratory depression or other undesired consequences caused by narcotic overdosage. In further support of the present disclosure, the following references are hereby incorporated by reference in their entireties: U.S. Pat. No. 5,957,885 to Bollish et al., U.S. Pat. No. 7,565,905 to Hickle, U.S. Pat. No. 7,668,731 to Martucci et al., U.S. Pat. No. 7,398,115 to Lynn, and U.S. Pat. No. 7,081,095 to Lynn et al.

One substance for counteracting the effects of narcotics is a known agent called naloxone, which has been in existence since 1971. Naloxone is frequently used in, for example, emergency and first responder situations to treat/reverse a known or suspected narcotic overdose resulting in impending or actual respiratory arrest. Naloxone is known to take effect within less than one minute and is further known to be both inexpensive and effective at reversing narcotic effects, most importantly restoring normal breathing in patients. There is generally no substantial risk of overdose, side effects, and no reported allergies with the reversal agent. Generally speaking, naloxone is one of the safest drugs on the market. The most significant risk to the patient is that pain being treated will return. However, when weighed against a likelihood of death or brain injury, pain is relatively insignificant as a consequence to critical, life saving benefits provided by naloxone.

According to one embodiment, naloxone is provided in proper dosages by the apparatus, automatically, through the patient's pre-existing intravenous line in response to an alarm condition after detection by a monitoring apparatus, such as, by way of example but not limitation, an end-tidal $CO_2$ monitor. The delivery apparatus can be activated by one or more monitors adapted for continuously receiving information from the patient. Thus, delivery systems of the present invention obviate the need for various levels of unpredictable human interaction, such as dependency on a care-giver being present, human response to various indicia or prompts, and human interaction with a medication dispensing machine, for example. Reliance upon human intervention introduces delays into situations and environments where such delays are unacceptable, and have undisputably resulted in patient deaths and brain damage that are well-known.

Embodiments of the present invention also address the significant shortcomings of PCA pumps. Systems and methods of the present invention provide numerous benefits in the form of redesigned user interfaces, improved hospital operating procedures, minimizing programming errors and enhancing detection before patients are harmed.

A representation of the three components provided in a preferred embodiment would comprise: (1) an end-tidal $CO_2$ monitor sampling exhaled $CO_2$ next to the nose through a small tube alongside the nasal cannula delivering oxygen inside the nose, with the sampled exhaled $CO_2$ generating a wave form and respiratory rate that is displayed, recorded and sent to (2) a computer or equivalent structure running software that detects alarm conditions that sends a signal to (3) one or more existing syringe pumps that respond by injecting the life-saving naloxone or other drug-reversal agent in the patient's intravenous line and/or through the nasal cannula, the nasal cannula delivery mode being, in fact, a unique and separate embodiment itself.

It is expressly recognized that the present invention is not limited to a post-operative or any particular type of patient. Indeed, it is contemplated that the device may be used on any hospitalized patient and in various home patient situations. While it is contemplated that the financial cost of the device and associated components is to be relatively low, the risks associated with respiratory depression when compared to any conceivable cost for the device would seem to dictate in favor of widespread and ubiquitous use.

In various embodiments, the present invention has life-saving capability even in patients not being treated with narcotics intravenously with PCA pumps. For example, patients receiving oral opiate/narcotic medications may not be connected to a standard PCA or any pump at all. In such situations, features of the present invention may be employed to monitor a patient and/or alert relevant care-givers to overdose from these oral medications.

In one embodiment, a supply of naloxone given either intravenously or intra-nasally is accompanied by a generally harmless but notable and response-provoking intranasal stimulant. Such substances include, but are not limited to known "smelling salts," ammonium carbonate, and various other similar substances known to elicit a response from a patient or generally arouse consciousness. For example, a drug that specifically reverses the effect of benzodiazepines (e.g. Valium, Lorazepam, Versed), called Flumazenil/Romazicon, may be supplied by the present invention to reverse sedation caused by these benzodiazepines.

In various embodiments, the present invention comprises Automatic External Defibrillator ("AED") features adapted for communication with additional components (e.g. capnography components) of the present invention. It is known that AED devices are becoming more and more common and simplified AED devices are now pervasive in workout facilities, office buildings, nursing homes, as well as hospitals. It is contemplated that various AEDs (portable or otherwise) are integrated into systems and methods of the present invention. For example, in one embodiment, a system is provided comprising a monitoring device (e.g. capnography devices, end-tidal $CO_2$, pulse oximetry, etc.) which is adapted for communication with an AED device. In one particular embodiment, a monitoring device and/or computer or similar device adapted for receiving information from the monitoring device sends a signal to alert the AED that a detected respiratory arrest may in fact have been caused by a cardiac arrest and need to be evaluated and defibrillated by the AED. Upon receiving the signal from a monitoring device, computer, and/or signal processing device, the AED conveys an indication that its services are needed. For example, an AED may be provided with lights and/or the ability to produce audio signals, thus drawing attention and immediately conveying to a first responder or care-giver that the device is needed, thus saving precious time in the presence of emergency circumstances.

In an alternative embodiment, features of an AED such as electrodes are connected to a patient known to be at risk for certain heart conditions. The AED is further adapted to receive signals from a monitoring device and/or a signal processing device and, upon the existence of certain predetermined conditions, provide a corrective electrical stimulus to the patient. Accordingly, in this embodiment, AED treatment may be provided to a patient in need of the same without the need for specific human intervention.

Yet another embodiment of the apparatus might be deployed for home use scenarios, as in post-operative patients being sent home but who continue to need pain medications of the narcotic/opiate class, or in chronic pain or cancer patients requiring high doses of narcotics for pain control. These patients monitored at home could receive narcotic reversal agents through a nasal cannula, and not require an intravenous line to be running. Also, other stimulating methods could be used in patients with sleep apnea or other conditions not amenable to treatment with narcotic or benzodiazepine reversal agents, i.e., smelling salts via nasal cannula, audible or weak electrical stimuli, or even transcutaneous stimulation of the phrenic nerves in the neck that activate the diaphragm, causing artificially-induced inhalation and exhalation in completely unresponsive patients.

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. Further details and other features will become apparent after review of the following Detailed Description and accompanying drawing figures.

BRIEF DESCRIPTION OF THE DRAWINGS

Those of skill in the art will recognize that the following description is merely illustrative of the principles of the disclosure, which may be applied in various ways to provide many different alternative embodiments. This description is made for illustrating the general principles of the teachings of this disclosure invention and is not meant to limit the inventive concepts disclosed herein.

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein. In the drawings.

DETAILED DESCRIPTION

The present invention provides its benefits across a broad spectrum of endeavors. It is applicant's intent that this specification and the claims appended hereto be accorded a breadth in keeping with the scope and spirit of the invention being disclosed despite what might appear to be limiting language imposed by the requirements of referring to the specific examples disclosed. To acquaint persons skilled in the pertinent arts most closely related to the present invention, a preferred embodiment of the method that illustrates the best mode now contemplated for putting the invention into practice is described herein by, and with reference to, the annexed drawings that form a part of the specification. The exemplary method is described in detail without attempting to describe all of the various forms and modifications in which the invention might be embodied. As such, the embodiments described herein are illustrative, and as will become apparent to those skilled in the arts, can be modified in numerous ways within the scope and spirit of the invention, the invention being measured by the appended claims and not by the details of the specification.

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '________' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims) To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
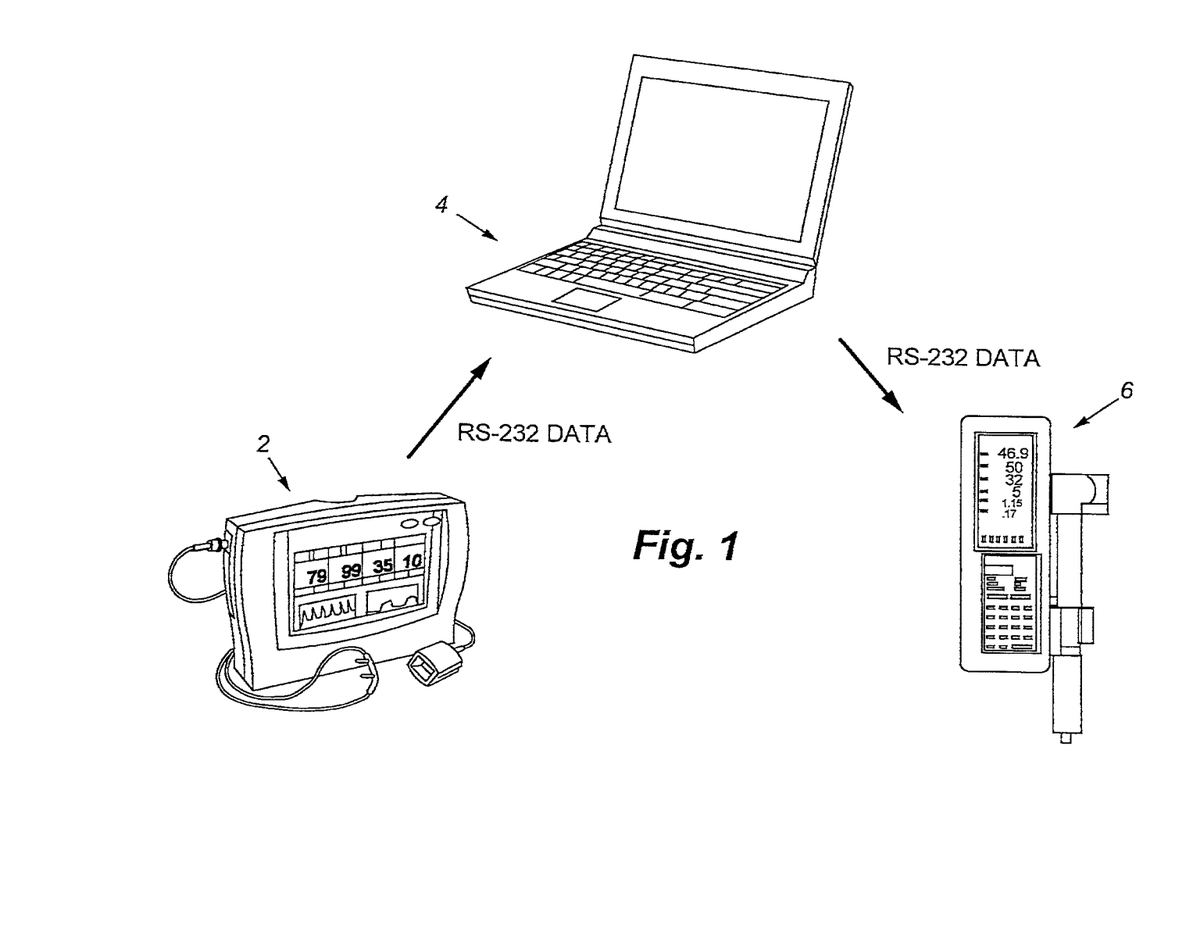
FIG. 1 is a system according to one embodiment of the present disclosure, comprising a $CO_2/SaO_2$ monitor, a tamper proof syringe pump and a notebook or laptop computer connected to the $CO_2/SaO_2$ monitor and the syringe pump for monitoring the $CO_2/SaO_2$ associated with a patient's breathing and for initiating the delivery of one or more narcotic reversing agents.
Figure 2:
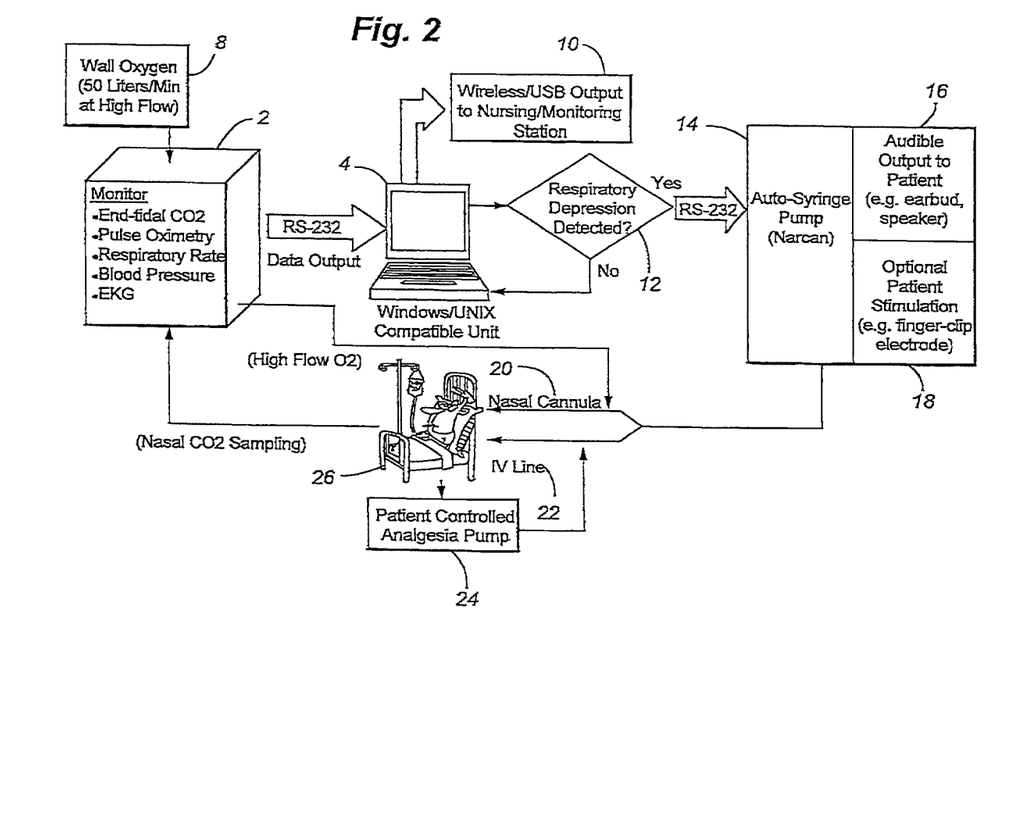
FIG. 2 is a schematic diagram of a system for monitoring a patient according to one particular embodiment of the present disclosure.
Figure 3:
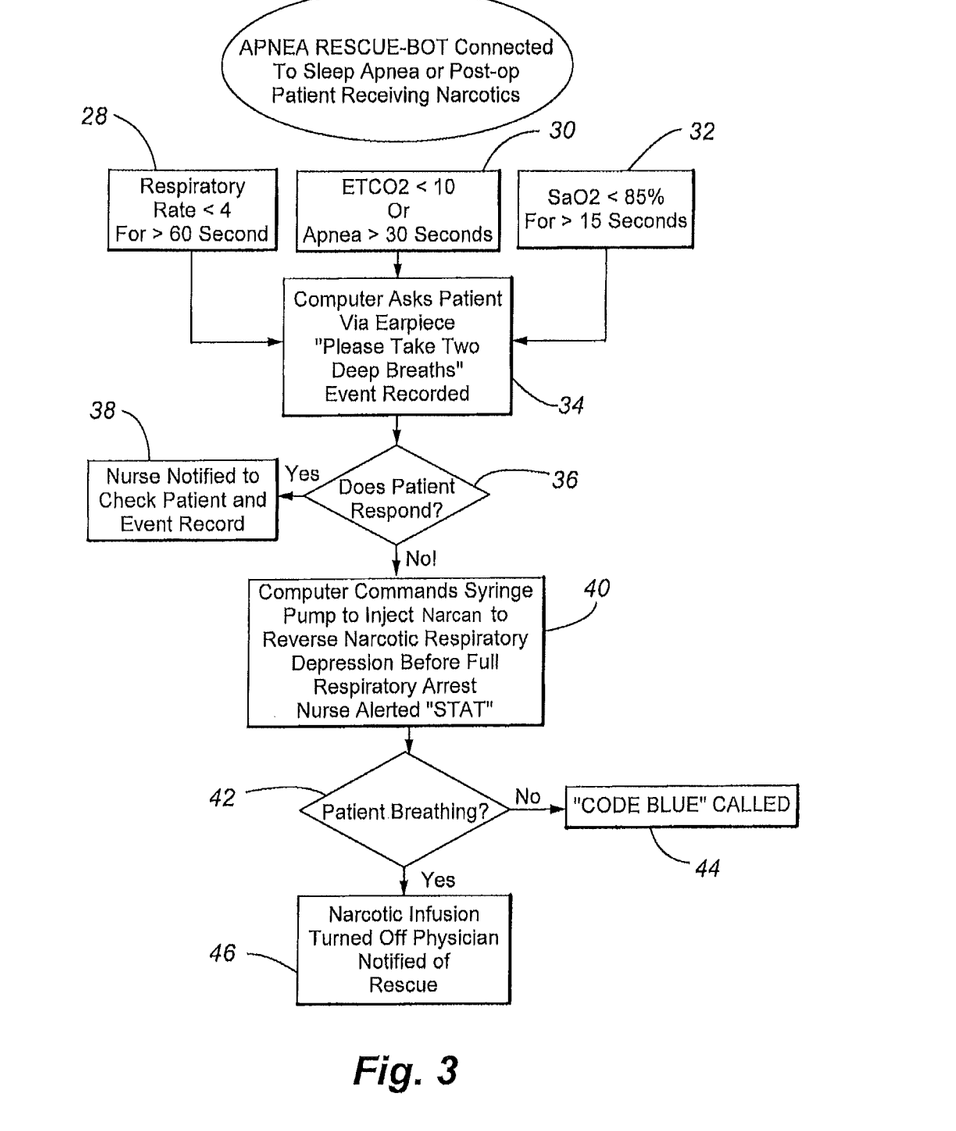
FIG. 3 is a flow chart of a method for monitoring a patient according to one particular embodiment of the present disclosure.

Reference is now made to the drawing figures, and in particular FIGS. 1-3. According to one embodiment of the present invention, a software-based system can provide the decision making capability to operate syringe pumps, which have been available for many years. In a preferred embodiment, all these devices (shown in FIGS. 1-3) can be combined in one device to provide a safer alternative for these patients. In one embodiment, the system operates in conjunction with a PCA pump apparatus. In an alternate embodiment, the system replaces the obsolete PCA pump apparatus.

Referring to FIG. 1, a representation of the three components provided in a preferred embodiment would comprise: (1) an end-tidal $CO_2$ monitor 2 sampling exhaled $CO_2$ next to the nose through a small tube alongside the nasal cannula delivering oxygen inside the nose, with the sampled exhaled $CO_2$ generating a wave form and respiratory rate that is displayed, recorded and sent to (2) a computer 4 or equivalent structure programmed to detect alarm conditions that sends a signal to (3) one or more existing syringe pumps 6 that respond by injecting the life-saving naloxone or other drug-reversal agent in the patient's intravenous line.

In another embodiment, the same naloxone reversal agent is separately and/or simultaneously delivered through a oxygen-supplying nasal cannula tube, as a nasal spray to be absorbed, either as the sole method of supplying the antidote, or as a fail-safe back-up mode in the event the intravenous line does not exist or is faulty. All these components could further be connected and made to function with the well-known RS-232 interface, for example.

FIG. 2 is a schematic view of the system components discussed above, wherein a series of steps is provided that typically occurs in a system according to a preferred embodiment. According to this embodiment, the naloxone is delivered by a syringe pump 14 or by way of a nasal cannula 20, or both. The nasal cannula 20, which delivers oxygen to the patient, also applies slight suction through a separate tube near the patient's nose, for monitoring exhaled $CO_2$ from the patient. Although the PCA pump is shown in FIG. 4, it is expressly understood that the system may operate in conjunction with such an apparatus, or in the complete absence of such an apparatus.

As shown, a patient monitoring unit 2 is provided in communication with a patient 26 and various system components. The patient monitoring unit 2 may be connected to a source of oxygen 8 for transmitting oxygen to a patient 26 through a nasal cannula 20. The patient monitoring unit 2 may further be connected to and adapted for transmitting patient related data to an interface unit 4, such as a laptop computer. In various embodiments, one or more interface units 4 are connected to and in communication with additional system components via known RS-232 cable(s). The interface unit 4 may comprise an output 10, such as a wireless signal and/or USB port for transmitting data to, for example, a nurse's station. One of skill in the art will recognize that the type of information that may be transmitted through an output 10 is not limited to any particular patient information or distress signal. Rather, the output 10 is adapted to convey any desired information that may be obtained from the patient monitoring unit 2.

In one embodiment, the interface unit 4 performs a detection step 12 wherein data received from the patient interface unit 2 is analyzed to determine whether or not respiratory depression may be occurring. In various embodiments, the step 12 is performed continuously. In one particular embodiments, the step 12 may be performed at predetermined intervals, the predetermined intervals being suitably short to be able to recognize a respiratory depression condition quickly (e.g. at least approximately every 15 seconds).

The interface unit 4 is further connected to and in communication with an auto-syringe 14 or pump. In one embodiment, this connection/communication is accomplished through RS-232 cable or similar devices including, for example, wireless devices. Upon a determination of patient condition in step 12 requiring action, such as respiratory depression, the auto-syringe pump automatically dispenses a predetermined quantity of naloxone to the patient through a nasal cannula 20 and/or an intravenous line 22. A patient 26 may additionally be provided with or connected to a PCA pump 24.

In various embodiments, the interface unit 4 is further adapted for communication with and activation of additional stimulating means. For example, in one embodiment the interface unit 4 is in communication with a device 16 for providing an audible signal to a patient, such as an ear piece adapted for producing a spoken and/or pre-recorded command to the patient 26. Furthermore, the interface unit 4 may be additional adapted for prompting or initiating additional patient stimulation including, but not limited to activation of a finger-clip electrode 18 and/or dispensing of smelling salts or similar stimulating means.

In one embodiment, features and devices of the present invention as described herein are packaged into a single unitary device. In an alternative embodiment, components are provided individually such that existing patient care facilities can be modified or updated with features of the present invention.

FIG. 2 depicts various embodiments, systems, and features which may be used alone or in combination with one another. Accordingly, the present invention is not limited to any particular arrangement(s) as shown in FIG. 2. For example, where FIG. 2 depicts an auto-syringe pump 14, an audible output feature 16, an optional patient stimulator 18, a nasal cannula 20, and an intravenous line 22 for dosing a patient, these and various other features may exist alone or in combination with one another in various embodiments of the present invention.

The flow chart shown in FIG. 3 indicates that in one embodiment of the present disclosure, labeled "Apnea Rescue-Bot," is connected by one or more input devices, which in turn are capable of receiving inputs from a post-operative patient receiving narcotics in order to detect alarm conditions 28, 30, 32. Alarm conditions might be, for example, a respiratory rate less than 4 for more than 60 seconds 28, an end-tidal $CO_2$ absolute level less than 10 (normal 25), apnea (no breathing) for greater than 30 seconds 30, or pulse oximetry less than 85 percent for greater than 15 seconds 32. These or similar alarm conditions may first trigger the computer to request the patient audibly to take a deep breath 34. In one embodiment, a response detection step 36 is provided. If no first response improved or changed the alarm state, step 40 is initiated wherein hospital staff would be notified to check the patient in any or all of various ways, depending on the alarm conditions initiated actions by the "Apnea Rescue-Bot." Either accompanying or following the audible command attempt to encourage breathing, a weak electrical stimulus may also be delivered by, for example, a separate 9-volt battery via wires connected to ordinary adhesive EKG pads. If the patient did not breathe normally in response to audible or electrical stimulus, the computer, according to this embodiment, would elevate the severity of the alarm condition and command the syringe pump to inject naloxone to reverse respiratory depression systems before cardio-pulmonary arrest, brain injury or death.

In one embodiment, an additional monitoring step 42 is provided wherein, in the absence of detection of satisfactory patient conditions, overhead paging for "Code Blue" 44 is accomplished by hard-wired, USB, or wireless connection to the paging system at the hospital. Nurses responding immediately to check would often find the patient waking up and breathing again because of the short time naloxone takes to reverse narcotic effects on breathing and consciousness. Alternatively, if the patient had not responded by the time the nurse reached the patient a "Code Blue" would already have been called, summoning all available help to resuscitate the patient.

In one embodiment, wherein the patient does respond favorably to prompts contemplated at step 34, the system provides a notification 38 to nurse, staff, or care-givers to verify the patient's status and take any appropriate actions. In one embodiment, where appropriate patient conditions are detected at step 42, narcotic delivery is suspended at step 46 and care-givers are notified of the incident. In a particular embodiment, notification is provided via a written report produced by the interface or computer. The written report may comprise various vital information, such as time of incident, patient conditions which triggered action, actions taken, and advice regarding subsequent patient monitoring and/or treatment.

The invention described above may come in a number of various configurations. It could be conceived of as a sophisticated PCA infusion pump, such that it would have self-correcting "reverse capability" or narcotic effect reversal, with or without "braking" or stopping of the narcotic delivery itself. These benefits would make stand-alone narcotic infusion pump technology without narcotic reversal capability obsolete, because the invention would include not only the best available monitoring capability to detect respiratory threats, but it would include the first and only automated rescue delivery system to provide emergency administration of the remedy.

It is also contemplated that the present invention could include multiple monitoring modalities, such as blood pressure, EKG monitoring, or it could be used in the emergency department or anywhere patients are given sedatives for, by way of example but not limitation, colonoscopies, procedures in radiology, heart cath labs, and any place outside the operating room where they are continuously watched by anesthesiologists, the ultimate experts and inventors of critical care medicine.

Even though one of the invention uses would be for addressing problems with patients receiving narcotics, it is to be expressly understood that the invention could also be used in sleep apnea patients not being given narcotics. In various embodiments, the present invention provides an audible or electrical encouragement to breathe upon detecting the relevant patient condition, and simultaneously employs high-flow oxygen, which is known to provide beneficial and stimulating results. In one embodiment, the invention receives high-flow oxygen directly from the hospital wall source or a portable oxygen supply, and comprises its own internally adjustable valve. Thus, in at least one embodiment, in response to alarm conditions, the present invention immediately administers high-flow oxygen both as a stimulus to breath and as a way to deliver the naloxone reversal in spray form through the nasal oxygen supply cannula.

According to one embodiment, the invention comprises approximately 6-10 different resuscitation drugs together in a multi-compartment cassette, for use in critical cardiac arrest situations or very unstable patients. In a particular embodiment, the cassette contains naloxone, D50 glucose, epinephrine, atropine, phenylephrine, vasopressin, esmolol, cardizem, and adenosine. Such a multi-compartment cassette could address chaotic scenarios in ERs and other places where nurses are scrambling to locate these drugs, potentially rummaging through carts for these drugs, tearing open boxes, assembling syringe cartridge/injectors, looking for needles and syringes to suck drugs out of vials, etc. prior to the patient actually getting the needed drug.

According to one particular embodiment, drugs could come pre-loaded in a manually or automatic multi-injector that could be overridden by physicians, or used before the arrival of higher-level personnel trained in resuscitation.

There are several commonly used drugs in resuscitation scenarios, and much time and effort could be saved by having such drugs pre-packaged, so that a staff member could simply press one button, and the device, which is already plugged into the patient's IV, could deliver the intended resuscitation drug. Possible drugs include but are not limited to naloxone (reverse narcotic), D 50 (sugar to reverse insulin overdose), $NaHCO_3$/bicarb (to reverse high potassium and acidosis), Romazicon/flumazenil (to reverse Versed and Valium), glycopyrrolate (Robinul) or atropine (to speed up a slow heart), phenylephrine (to safely increase blood pressure without speeding up the heart), epinephrine/adrenalin (to raise the blood pressure and speed up the heart, facilitate defibrillation, treat shock and severe allergic reaction and shock), Esmolol (safe short acting drug to slow down the heart), Vasopressin (powerful drug for severe shock), and Cardizem and Adenosine to slow rapid heart rhythms, In the event of a failed or unobtainable intravenous access, the device could also permit some or all of the drugs to be delivered intra-nasally. For example, in various embodiments, naloxone and other drugs are provided through a nasal cannula, either in addition to or in lieu of intravenous delivery. As it is known that naloxone presents little to no risk of adverse effects or overdose, a particular embodiment contemplates administering naloxone or similar agents through an intravenous and intra-nasally.

According to a preferred embodiment, naloxone is pre-loaded in a proprietary tamper-proof cassette or syringe-injector. The preferred way to use the injector would be with the proprietary naloxone loads, to avoid it being used for any other purpose (naloxone is harmless if injected rapidly, and other medications could be harmful if delivered fast in a non-proprietary user-accessible device). The injector could deliver intravenously and/or intra-nasally through nasal oxygen cannula plugged into the Apnea Rescue-Bot in response to Apnea Condition.

The device could provide further an assessment of pain control based on respiratory rate or quality of end-tidal $CO_2$ tracing, and advise whether the patient could safely tolerate more narcotic without respiratory depression, thus improving both comfort and the safety of patients. For example, respiratory rates greater than 20 with a high quality capnograph tracing would allow an increase in narcotic dosing, and could advise the nurse, or alternately allow the patient more frequent opportunities to self-medicate safely, without demanding more of nursing personnel. Voice-activated patient requests could be evaluated and decided upon by the device if respiratory parameters were reasonable and no alarm conditions were being approached. According to this embodiment, all actions, alarms, and adjustments would be recorded, displayed, automatically entered into the EMR (Electronic Medical Record) or wirelessly relayed to the nursing station if desired.

In another embodiment of the device, other therapeutic medications besides naloxone could be given intravenously or intra-nasally. For example, phenylephrine, used commonly as a vaso-constrictor to relieve nasal congestion is well known to have the side-effect of elevating blood pressure. This side effect could be exploited as a remedy for dangerously low blood pressure with nasal administration of the antidote, at least until an intravenous line could be established for the best support of low blood pressure. In addition, dangerously slow heart rates could be safely raised with dosages of glycopyrrolate or atropine, dangerously fast heart rates could be slowed with Esmolol (which is metabolized in several minutes), and dangerously high blood pressure could be lowered with any number of medications intra-nasally in judicious amounts. Thus, the invention has another embodiment as a "Critical Care Rescue-Bot," which may supply the necessary dosages either intravenously or intra-nasally (in the event of intravenous line failure or prior to establishing an intravenous line, which occurs commonly).

According to varying embodiments described herein, the system and apparatus described above may all be controlled by a control system, such as a programmable logic controller or relay-based control system, with accompanying algorithms to govern the relationship between the monitoring inputs, the events or conditions and subsequent reporting or alarming for notification to hospital staff or other caregivers, as well as the actual automation of the various drugs being supplied to the patient. Such control systems that are now known or developed in the future are contemplated with and considered within the scope of the present disclosure.

It is to be expressly understood that uses for capnography monitoring devices and its rescue-oriented technology, other than the uses described above, are contemplated for use with the apparatus and method of the present disclosure. The device could easily be used in home health scenarios, for example. As described above, there could be a very basic device for patients with sleep apnea. Currently, patients use CPAP machines (continuous positive airway pressure machines) with tightly fitting masks to force oxygen through obstructed and collapsed airways, and it would be advantageous to have a monitoring capability on these machines that could stimulate them audibly or electrically. In various embodiments, features of the present invention including, but not limited to naloxone delivery, may be provided through known CPAP machines.

In various embodiments, less severe types of sleep apnea are treated with extra oxygen by nasal cannula, and built-in monitoring is provided with presently available $CO_2$, monitoring nasal cannula. In this embodiment, there is generally no need for naloxone reversal injection or nasal spray capability, with the possible exception of smelling salts.

In various embodiments of the present invention, home health systems and features are provided. For example, patients who may generally qualify for discharge from a primary care facility (e.g. hospital), yet mat still be at risk for over-sedation with prescribed narcotic-opiate pain pills, and chronic pain or cancer patients requiring administration of narcotics could be monitored and/or treated in situations outside of a hospital or primary care facility with various embodiments of the present invention. For example, it is contemplated that a scaled-down version of the invention may be provided wherein an oxygen source comprises a portable oxygen tank rather than a wall-source, and various additional system components as shown and described herein are provided in sizes and formats adapted for home use.

In various embodiments, a system is provided comprising the ability to meter, monitor, and/or detect the amount of a narcotic dispensed to a patient. In one embodiment, data related to the amount of a narcotic or pain-relieving drug provided to a patient (e.g. through a PCA pump) is continuously monitored and automatically compared with relevant patient information such as age, weight, gender, etc. Relevant patient information may be manually input into the system, such as through manual data entry at a terminal or interface upon check-in or admittance to a hospital. Alternatively, relevant patient information may be automatically obtained from pre-existing medical records. In one embodiment, a system is provided with predetermined limits for various types of dispensed drugs and related patient information. In this embodiment, when the predetermined limits are exceeded, dispensing of drugs is at least temporarily prevented and/or naloxone or other reversal agents are dispensed to the patient.

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g. the use of a certain component described above alone or in conjunction with other components may comprise a system, while in other aspects the system may be the combination of all of the components described herein, and in different order than that employed for the purpose of communicating the novel aspects of the present disclosure. Other variations and modifications may be within the skill and knowledge of those in the art, after understanding the present disclosure. This method of disclosure is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system configured to monitor and treat respiratory depression comprising:
   a patient monitoring unit configured to monitor at least one patient condition(s) and to output a signal;

an interface unit including a microprocessor and a user interface configured to provide an interface for at least one user, wherein the interface unit is in communication with the patient monitoring unit;

a first device for dispensing at least a narcotic;

a second device configured to automatically dispense at least one dosage of a narcotic reversal agent in response to at least the signal from the patient monitoring unit, the signal indicating at least one patient condition is outside a preset condition value; and wherein the interface unit is configured to continuously receives information from the patient monitoring unit after dispensing at least one dosage of a narcotic reversal agent, and wherein the interface unit is configured to signal the first device for dispensing at least a narcotic to be suspended when appropriate patient conditions are detected.

2. The system of claim 1, wherein the at least one patient condition is selected from the group consisting of: a respiratory rate, a carbon dioxide, oxygen and pH value, a blood pressure, an acoustic measurement of respiration, a heart rate, a physiological response and a response to an audible signal.

3. The system of claim 1, wherein the interface unit is selected from the group consisting of: a laptop computer, a desktop computer, a tablet, a mobile device, a cellular telephone, a pager and a portable desktop accessory.

4. The system of claim 1, wherein the narcotic reversal agent comprises naloxone and is provided to a patient intravenously.

5. The system of claim 1, wherein the second device configured to automatically dispense the narcotic reversal agent comprises a pump and a nasal cannula, wherein the narcotic reversal agent comprises naloxone in spray form dispersed in an oxygen stream, and is provided to the patient intranasally.

6. The system of claim 1, wherein the second device configured to automatically dispense the narcotic reversal agent comprises:

a first pump and a nasal cannula, wherein the narcotic reversal agent comprises naloxone in spray form dispersed in an oxygen stream, and is provided to the patient intranasally; and a second pump, wherein the narcotic reversal agent comprises naloxone in liquid form and is provided to the patient by an intravenous line.

7. The system of claim 6, wherein the first pump is dedicated to the delivery of the narcotic reversal agent, which releases the at least one dosage of the narcotic reversal agent upon receiving the signal from the patient monitoring unit, wherein the controlled dosage is at least based on the signal.

8. The system of claim 1, wherein the second device configured to automatically dispense the narcotic reversal agent releases the narcotic reversal agent upon receiving the signal from the patient monitoring unit and a second signal from the interface unit.

9. The system of claim 6, wherein the first pump is independent of the first device for dispensing at least a narcotic to a patient.

10. The system of claim 1, wherein the first device for dispensing at least a narcotic comprises a pump, wherein the at least a narcotic is dispensed via an intravenous line.

11. The system of claim 1, further comprising a stimulation device for applying at least one stimulus to the patient comprising at least one of a low voltage electrical stimulus applied to the skin, an audible alarm, a means for dispensing smelling salts, a means for transcutaneous stimulation of the phrenic nerve, and combinations thereof.

12. The system of claim 1, wherein the patient monitoring unit triggers an alarm when the at least one patient condition is outside the preset condition value, wherein the present condition value is at least one of a respiratory rate less than about 4 for more than about 60 seconds, an end-tidal $CO_2$ absolute level less than about 10, apnea for greater than about 30 seconds, a pulse oximetry less than about 85 percent for greater than about 15 seconds, and combinations thereof.

13. The system of claim 1, wherein the patient monitoring unit triggers an alarm when the at least one patient condition is outside the preset condition value, wherein the alarm is communicated to a care-giver via a paging system.

14. The system of claim 1, wherein the interface unit communicates information comprising at least one of the at least one patient condition, narcotic reversal agent dispensing rates, narcotic dispensing rates, alarm conditions, and combinations thereof to at least one of an electronic medical record, a nursing station, and combinations thereof.

15. The system of claim 14, wherein the information communicated is stored, displayed, or both, at the electronic medical record, the nursing station, or both.

16. The system of claim 14, wherein the information communicated is transferred wirelessly.

17. A system configured to monitor and treat respiratory depression in a human patient comprising:

at least one patient monitoring unit configured to monitor at least one patient condition and to output a signal when the at least one patient condition approximates a predetermined danger level;

an interface unit including a microprocessor and a user interface configured to provide an interface for at least one user, wherein the interface unit is in communication with the patient monitoring unit;

a first device for dispensing at least a narcotic;

a second device configured to automatically dispense at least one dosage of a narcotic reversal agent in response to at least the signal from the patient monitoring unit; and a stimulation device configured to apply at least one stimulus to the patient comprising at least one of a low voltage electrical stimulus applied to the skin, an audible alarm, a means for dispensing smelling salts, a means for transcutaneous stimulation of the phrenic nerve, and combinations thereof, wherein the interface unit is configured to signal application of the at least one stimulus to the patient and to continuously receive information from the patient monitoring unit after dispensing at least one dosage of a narcotic reversal agent, and wherein the interface unit is configured to signal the first device for dispensing at least a narcotic to be suspended when appropriate patient conditions are detected.

18. The system of claim 17, wherein the second device configured to automatically dispense at least one dosage of a narcotic reversal agent comprises:

a first pump and a nasal cannula, wherein the narcotic reversal agent comprises a spray dispersed in an oxygen stream, and is provided to the patient intranasally; and a second pump, wherein the narcotic reversal agent comprises a liquid, and is provided to the patient by an intravenous line.

19. The system of claim 17, wherein the first device for dispensing at least a narcotic comprises a third pump wherein the at least a narcotic is dispensed via an intravenous line.

* * * * *